US006786902B1

(12) United States Patent
Rabin et al.

(10) Patent No.: US 6,786,902 B1
(45) Date of Patent: *Sep. 7, 2004

(54) METHOD AND APPARATUS FOR CRYOSURGERY

(75) Inventors: Yoed Rabin, Pittsburgh, PA (US); Thomas Benjamin Julian, Pittsburgh, PA (US); Norman Wolmark, Pittsburgh, PA (US)

(73) Assignee: Allegheny-Singer Research Institute, Pittsburgh, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/527,491

(22) Filed: Mar. 16, 2000

Related U.S. Application Data

(63) Continuation of application No. 08/668,692, filed on Jun. 24, 1996, now Pat. No. 6,039,730.

(51) Int. Cl.$^7$ .............................................. A61B 17/36
(52) U.S. Cl. ............................. 606/23; 606/21; 606/22; 128/898
(58) Field of Search .............................. 606/20, 21, 22, 606/23, 24, 25, 26; 378/37; 128/898

(56) References Cited

U.S. PATENT DOCUMENTS

| 3,889,680 | A | * | 6/1975 | Armao | 606/23 |
| 5,386,447 | A | * | 1/1995 | Siczek | 378/37 |
| 5,520,682 | A | * | 5/1996 | Baust et al. | 606/24 |
| 5,647,868 | A | * | 7/1997 | Chinn | 606/21 |

* cited by examiner

Primary Examiner—Rosiland K. Rollins
(74) Attorney, Agent, or Firm—Ansel M. Schwartz

(57) ABSTRACT

The present invention pertains to an apparatus for cryosurgery. The apparatus comprises a cryoneedle having a diameter less than 3.2 mm. The apparatus is also comprised of a thermal insulation shell disposed about a portion of the cryoneedle for reduction of heat transfer from surrounding tissues or freezing prevention of surrounding tissues during application of the cryoneedle with the shell. The cryoneedle and shell are configured for insertion into a body of a patient. The present invention pertains to a method for freezing tissues. The method comprises the steps of bringing into contact a cryoneedle having a diameter of less than 3.2 mm with a patient's body. Next, there is the step of flowing the cryofluid through the cryoneedle.

14 Claims, 6 Drawing Sheets

METHOD AND APPARATUS FOR CRYOSURGERY

This application is a continuation of application Ser. No. 08/688,692 filed on Jun. 24, 1996 now U.S. Pat. No. 6,039,730.

FIELD OF THE INVENTION

The present invention is related to cryosurgery. More specifically, the present invention is related to a method and apparatus for cryosurgery involving a cryoneedle having an outlet tube adjacent an inlet tube for cryofluid which cools the cryoneedle.

BACKGROUND OF THE INVENTION

This invention relates to minimally invasive cryosurgery. More particularly, this invention concerns the structure and the method of operation of a cryosurgical apparatus, which consists of one or more cryoprobes and a pressurized cryofluid source.

Cryosurgery, or the destruction of undesired biological tissues by freezing, has long been accepted as an important alternative technique of surgery (Orpwood, 1981; Rubinsky and Onik, 1991; Gage, 1992). Compared with conventional means of destroying tissues, such as surgical excision, radiotherapy and chemotherapy, visceral cryosurgery (especially minimal-invasive cryosurgery) offers the following potential advantages: simplicity of the procedure, minimal bleeding, anaesthetic effect of low temperatures, short period of patient recovery, low cost, minimal scarring, and possible stimulation of the body's immune system.

James Arnott, an English physician, was the first to introduce the technique of destruction of biological tissues by freezing in 1865. Since Arnott's first report, numerous cryodevices and techniques have been suggested. These have included pre-cooled metal blocks, spray/pour freezing with compressed or liquefied applications, cryogenic heat pipes, Joule-Thompson effect based cryoprobes and boiling effect based cryoprobes. However, as a result of the high cooling power usually needed for cryosurgery, and especially of internal organs, the boiling effect and the Joule-Thompson effect have been found to be the preferable cooling technique by most cryosurgeons.

Minimally invasive cryosurgery is monitored by ultrasound, CT or MRI; however, ultrasound is the most accepted imaging technique among cryosurgeons today. Utilizing these techniques, the cryosurgeon inserts the cryoprobe(s) into the region to be cryotreated. Then, the cryosurgeon activates the cryoprobe(s) according to a cooling protocol and monitors the frozen region growth (which is also termed "ice-ball"). When the undesired tissues are completely frozen, or when there is a danger of cryodestruction to important surrounding tissues, the cryosurgeon terminates the cooling process and the thawing stage follows. In some cases the cooling/thawing stages are repeated in order to increase cryodestruction.

The application of minimal-invasive cryosurgery calls for: a cryoprobe insertion technique that causes minimal damage to the surrounding healthy tissues, an accurate localization of the cryoprobe tip, and a precise monitoring of the frozen region formation. These criteria have served as the motivation for the continued efforts toward the reduction of cryoprobe diameter and improvement in imaging techniques. Ultimately, the cryoprobe diameter is a result of the diameter of the cryofluid tubes and by the cryoprobe's thermal insulator thickness. Since a typical cryoprobe diameter is relatively large, a pathway must be provide for the cryoprobe into the cryotreated region. An alternative solution for this problem is given by the invention presented hereby.

SUMMARY OF THE INVENTION

The objective of the invention is to provide a method and apparatus for minimal-invasive cryosurgery. More particularly, the objective of the invention is to provide a method and a cryoprobe that minimize the damage caused to the surrounding tissues due to either preparations for the cryoprocedure or cryoprobe penetration.

Another objective of the invention is to provide a method and cryoprobe that will enable a precise localization of the cryotreatment.

A further objective of the invention is to provide a simplified and compact apparatus for cryosurgery.

The present invention pertains to an apparatus for cryosurgery. The apparatus comprises a cryoneedle having a diameter less than 3.2 mm. The apparatus is also comprised of a thermal insulation shell disposed about a portion of the cryoneedle for reduction of heat transfer from surrounding tissues or freezing prevention of surrounding tissues during application of the cryoneedle with the shell. The cryoneedle and shell are configured for insertion into a body of a patient.

The present invention pertains to a method for freezing tissues. The method comprises the steps of inserting a cryoneedle having a diameter of less than 3.2 mm into a patient's body. Next, there is the step of flowing the cryofluid through the cryoneedle.

BRIEF DESCRIPTION OF THE DRAWINGS

In the accompanying drawings, the preferred embodiment of the invention and preferred methods of practicing the invention are illustrated in which:

FIG. 5.a insertion of cryoneedle 1 using an imaging device and a localization technique (such as ultrasound and stereotactic localization technique, respectively); FIG. 5.b insertion of thermal insulation shell 4; FIG. 5.c completion of the cryoprobe assembly and connection to a pressurized cryofluid source.

FIG. 6.a first the ends are cut at an angle $\phi$; and then FIG. 6.b the tube's tips are bent, one towards the other. Finally the tube's walls, 35 and 36, are welded together in a way that will allow fluid flow from one tube to the other.

DESCRIPTION OF THE PREFERRED EMBODIMENT

Figure 1:
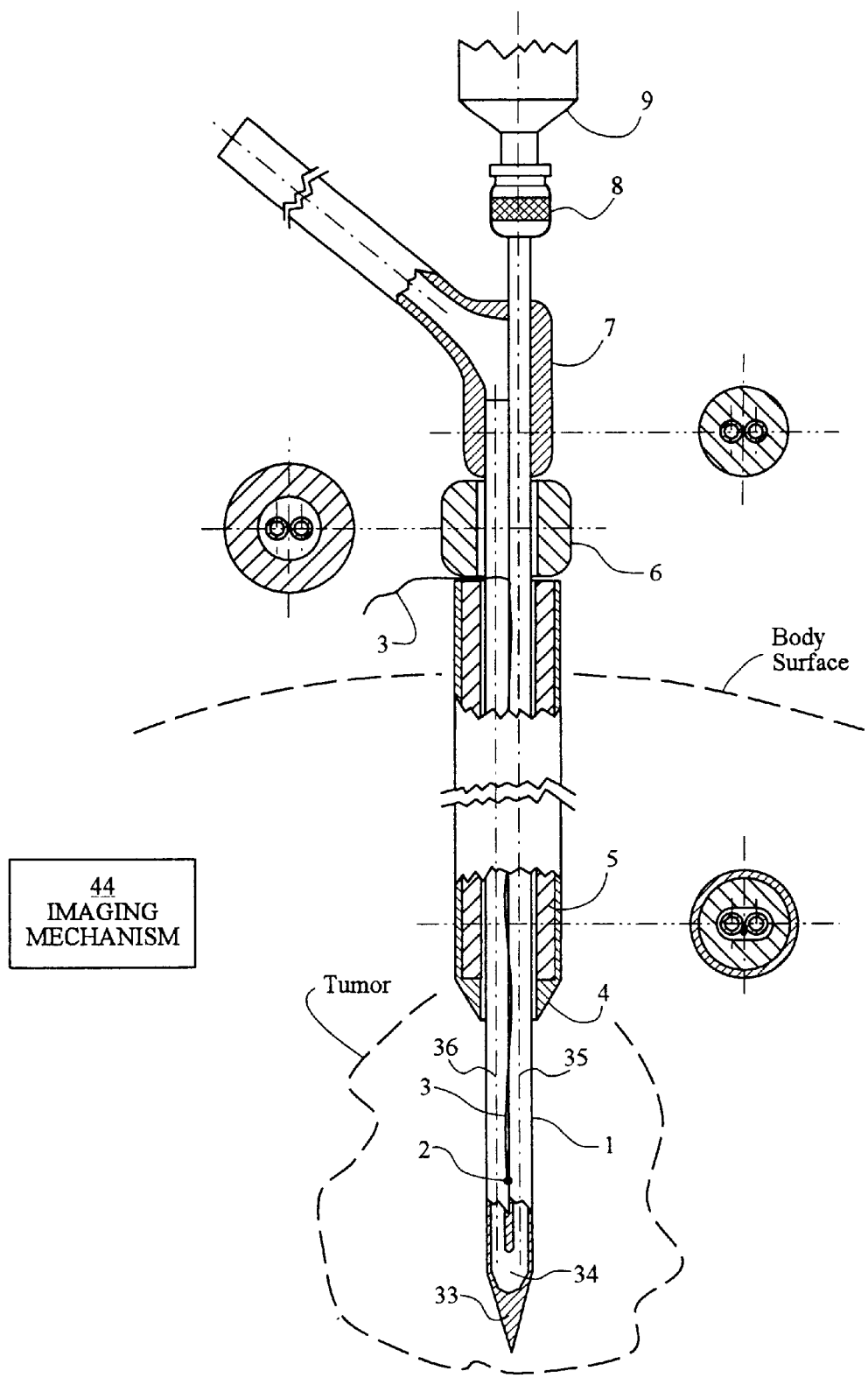
FIG. 1 is a side view of the cryoprobe A of the invention.

Referring now to the drawings wherein like reference numerals refer to similar or identical parts throughout the several views, and more specifically to FIGS. 1–4 thereof, there is shown an apparatus 100 for cryosurgery. The apparatus 100 comprises a cryoneedle 1 having a diameter less than 3.2 mm. The apparatus 100 is also comprised of a thermal insulation shell 4 disposed about a portion of the cryoneedle 1 for reduction of heat transfer from surrounding tissues, or freezing prevention of surrounding tissues, during application of the cryoneedle 1 with the shell 4. The cryoneedle 1 and shell 4 are configured for contact with and preferably insertion into a body of a patient.

Preferably, the cryoneedle 1 has a tip 33. Preferably, the tip 33 is pointed. Additionally, the apparatus 100 preferably includes a protection tube 6 for protection of an operator's hand during application of the cryoneedle 1. The shell 4 is disposed between the protection tube 6 and the tip 33. The protection tube 6 is disposed about the cryoneedle 1 and configured with the cryoneedle 1 and the shell 4 to be outside the body when the cryoneedle 1 and the shell 4 are inserted into the body of the patient during application. The protection tube 6 and the shell 4 can be slidably attached to the cryoneedle 1 as is presented in FIG. 1. Alternatively, the insulation shell 4 can be rigidly connected to the cryoneedle 1 as is presented in FIG. 2. The cryoneedle 1 preferably has an inlet tube 35 through which cryofluid flows during application of the cryoneedle 1 to the tip 33 and an outlet tube 36 through which cryofluid flows during application of the cryoneedle 1 from the tip 33. The outlet tube 36 preferably has a vent tube 7 which releases the cryofluid to the environment. Preferably, the cryoneedle 1 has a bridging connector portion, such as unshaped channel connector portion 34 disposed in conjunction with the tip 33 and connected with the inlet tube 35 and the outlet tube 36 to connect the inlet tube 35 and the outlet tube 36 and to allow cryofluid to flow from the inlet tube 35 to engage the tip 33 and flow out to the outlet tube 36. The inlet tube 35 preferably has an inside diameter between 0.8 mm and 2 mm. The outlet tube 36 preferably has an inside diameter between 0.8 mm and 2 mm. Preferably, the inlet tube 35 is in parallel with the outlet tube 36 and the inlet tube 35 is attached to the outlet tube 36.

Figure 6:
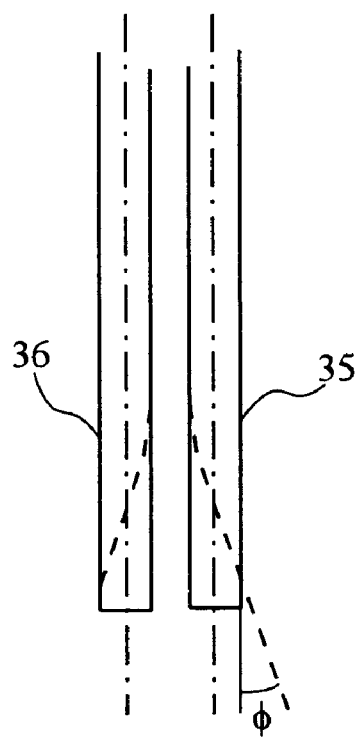
FIG. 6 is a schematic representation of the construction of the cryoprobe tip.
Figure 6:
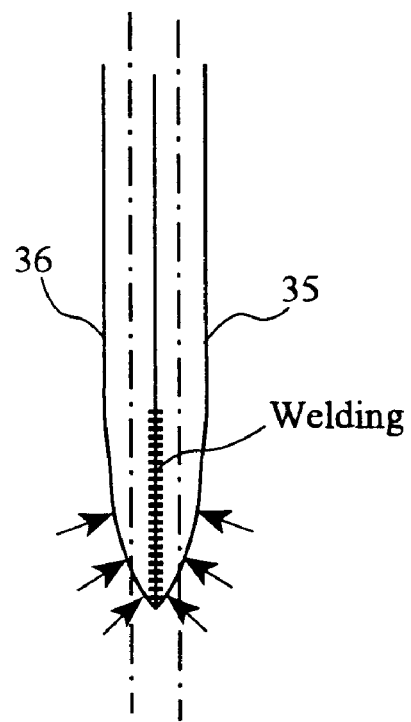

The tip 33 is formed by taking two separate tubes and cutting their ends at an angle of about 15°, as shown in FIG. 6a. The cut angled ends are then connected, for example, by being soldered or welded together to form the tip 33, as shown in FIG. 6b.

The apparatus 100 preferably includes a pressurized cryofluid source mechanism 30 connected to the inlet tube 35 via feeding tube 9 for providing pressurized cryofluid to the inlet tube 35. The pressurized cryofluid source mechanism 30 preferably includes a container 11 of cryofluid connected to the feeding tube 9. The pressurized cryofluid source mechanism 30 preferably also includes a tank 15 of pressurized gas connected to the container 11 to pressurize the cryofluid in the container 11. Additionally, the source mechanism 30 preferably includes a pump 31 connected to the tank 15 to pressurize the tank 15. The source mechanism 30 preferably also includes a control valve 10 disposed on the feeding tube 9 to control the flow of cryofluid from the container 11.

Additionally, the apparatus 100 preferably includes a temperature sensor mechanism 40 in contact with the cryoneedle 1 adjacent the tip 33 for sensing the active surface temperature of the cryoneedle 1. The temperature sensor mechanism 40 preferably includes a temperature sensor 2 disposed adjacent the tip 33 and in contact with the cryoneedle 1. The temperature sensor mechanism 40 preferably also includes sensor wires 3 connected to the sensor 2 and extending from the sensor 2. Furthermore, the temperature sensor mechanism 40 preferably includes a temperature measurement unit 22 connected to the sensor wires 3 for identifying the temperature sensed by the sensor 2.

The apparatus 100 can also include an imaging mechanism 44 for managing the cryoneedle 1 as it penetrates into the body of a patient. The apparatus 100 can also include at least a second cryoneedle 1 and a second thermal insulation shell 4 disposed about a portion of the second cryoneedle 1, as is presented in FIG. 4. The second cryoneedle 1 is connected to the source mechanism 30.

The present invention pertains to a method for freezing tissues. The method comprises the steps of bringing into contact and preferably inserting a cryoneedle 1 having a diameter of less than 3.2 mm with or into a patient's body. Next, there is the step of flowing the cryofluid through the cryoneedle 1. Preferably, the cryofluid is vented to the environment.

Preferably, after the inserting step, there is the step of sliding an insulation shell 4 in place over a predetermined portion of the cryoneedle 1 in the body of the patient. After the sliding step, there is preferably the step of sliding a protection tube 6 in place over the cryoneedle 1 until it is adjacent to the shell 4. The protection tube 6 is outside the patient's body. In an alternative preference, the inserting step includes the step of inserting the cryoneedle 1 with an insulation shell 4 positioned about the cryoneedle 1 at a predetermined location simultaneously into the body of the patient. Additionally, the inserting step preferably includes the step of imaging the cryoneedle 1 as it is inserted into the patient's body.

In the operation of the preferred embodiment, an apparatus 100, which has a cryoprobe such as a cryoprobe A, as shown in FIG. 1, is comprised of three main components: a cryoneedle 1, a thermal insulation shell 4, and a protection tube 6. The cryoprobe is assembled during, and as a part of, the cryosurgical procedure, as will be described in detail hereafter. Cryoneedle 1 has a U shape configuration and a sharp pointed tip 33, which is made of very fine tubes. Cryoneedle 1 leads the cryofluid forward, from feeding tube 9, through the inlet tube 35 of cryoneedle 1, to the cryotreated region, and backward, through outlet tube 36, to vent tube 7. Insulation shell 4 surrounds a part of cryoneedle 1 to reduce heat transfer from the surrounding tissues to the cryoneedle. Insulation shell 4 contains thermal insulator 5. Protection tube 6 surrounds an other part of cryoneedle 1, adjacent to insulation shell 4 but outside of the body, to protect the operator's hands and to reduce heat transfer from the surroundings to the cryoneedle. Insulation shell 4 as well as protection tube 6 are free to slide axially along cryoneedle 1. Feeding tube 9 feeds cryoneedle 1 with pressurized cryofluid, which is connected by fitting 8 to the inlet tube 35 of cryoneedle 1. The cryofluid exits from cryoneedle 1 through flexible vent tube 7, which is preferably connected under a pressure fitting.

The tubing from the coolant container 11 to fitting 8 is made of stainless steel, but copper, brass, steel or any other metallic alloy is suitable. The stainless steel can guarantee flexibility in the cryogenic temperature range and a long life. Flexible metallic tubes have a unique configuration and are available for commercial usage. Some plastics are brittle materials at cryogenic temperature range and therefore are generally not suitable for this task. The feeding tube 9 should be insulated by vacuum in order to reduce heat losses between the coolant container 11 and the cryoprobe. The simplest way of constructing a flexible and vacuum insulated tube is by using two standard flexible tubes, one inside the other. The space between the tubes is then sealed by sealing, for example, welding, while the air in between the tubes is pumped out to achieve a vacuum between the inner and outer tubes. A diameter ratio of 1 to 2 between the inner and the outer flexible tubes is suitable.

The internal diameter of the inner flexible tube of the feeding tube 9 should be about 3 times the inner diameter of the cryoneedle tubes, for a single cryoprobe operation. This ratio should be increased to about 5 for a multi-cryoprobe operation. This large diameter of flexible tube is chosen to reduce pressure losses between the coolant container and the cryoprobe. It is noted that the heat losses from the feeding tube 9 increase with the diameter.

Cryoprobe A can actually work without the protection tube 6, which does not affect significantly the performance of the apparatus. Protection tube 6 is mainly used for safety reasons, to protect the cryosurgeon's hands. This tube should be made of a plastic material like Teflon or Plexiglass which have low thermal conductivities. Typical thermal conductivity value of plastics is about 0.1 W/m-° C.

Figure 3:
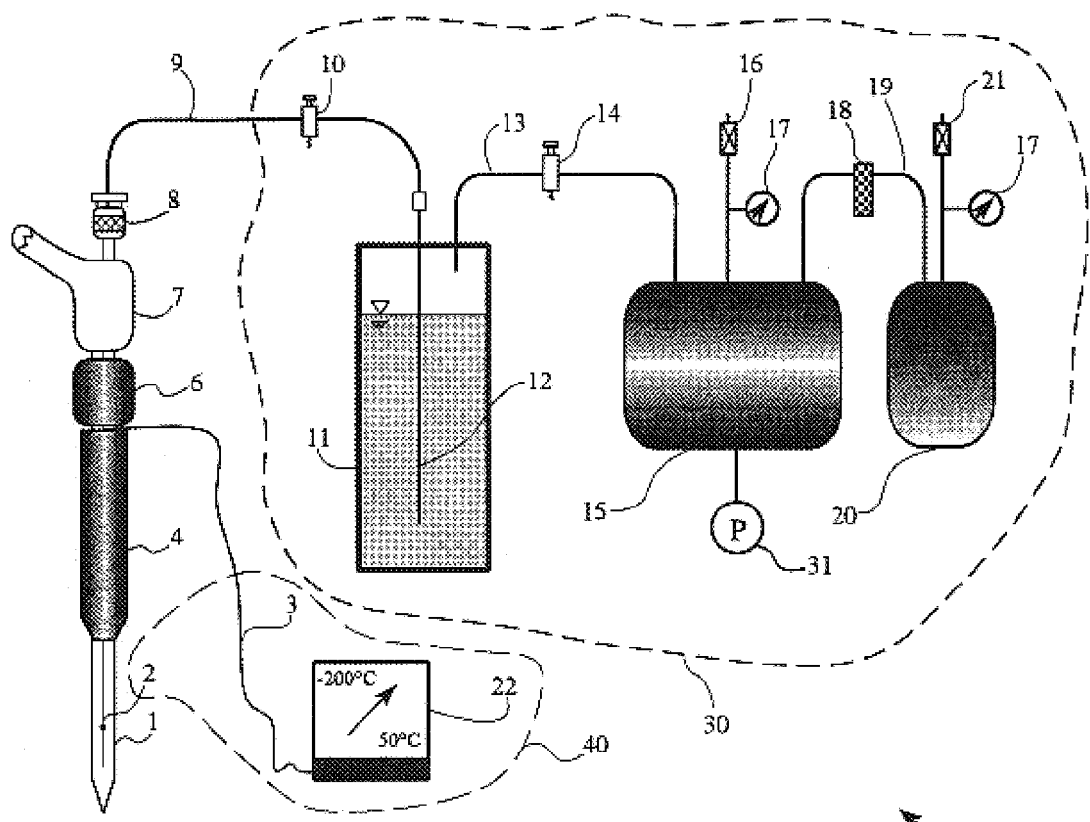
FIG. 3 is a schematic view of the cryosurgical apparatus with a single cryoprobe.

The cooling process in cryoprobe A takes place as follows. Cryofluid is forced from a cryofluid source into the cryoprobe through feeding tube 9. The cryofluid flows along cryoneedle 1 through the inlet tube 35 towards the cryoneedle tip 33 and then backwards through outlet tube 36 towards vent tube 7. Inside protection tube 6 and insulation shell 4, in both flow directions, the heat transfer from the surroundings and from the surrounding tissues, respectively, is minimal. The only significant heat transfer occurs where cryoneedle 1 is in direct contact with the tissue, and therefore this area is designated herein as the cryoprobe active surface. Downstream heat convection takes place along the cryoprobe active surface, with or without the boiling phenomenon inside the cryoneedle, and causes freezing of the undesired tissues. The temperature of the cryoprobe active surface is monitored by temperature sensor 2 and the signals are transferred through temperature sensor wires 3 to temperature measurement unit 22, as shown in FIG. 3. Monitoring of the temperature near the cryoprobe tip 33 is required for controlling the coolant (liquefied gas) flow rate. The temperature of the cryoprobe active surface, to which the temperature sensor is attached, is expected to be very close to the coolant boiling temperature at extremely high flow rates. The temperature is not expected to drop much while reducing the flow rate, until a certain point of which the boiling rate is higher than the flow rate and the flow of the liquefied coolant turns entirely into gas. The flow rate at which this phenomenon occurs is defined here as the critical flow rate; applying flow rates above the critical flow rate will result in a waste of coolant while applying flow rates below the critical flow rate will result in a significant reduction of the cooling power. Therefore, the temperature sensor at the cryoprobe tip 33 acts as a flow rate indicator, telling the operator to increase or decrease the coolant flow rate via control valve 10. The usage of a thermocouple as a temperature sensor 2 is convenient and inexpensive. The couples copper-constantan or iron-constantan are suitable for the cryogenic temperature range. The temperature measurement unit 22 is a standard unit that amplifies the thermocouple signal and translates them into temperature values. This unit should be able to operate between normal body temperature range, i.e. at least 40° C., down to the boiling temperature of the coolant, i.e. −196° C. for the liquid nitrogen case.

The cooling effect of the cryoneedle is achieved by a boiling phenomenon inside the cryoneedle's tubes. The boiling phenomenon, or liquid-gas phase change, takes place at a constant temperature and demands a relatively high energy, known as latent heat. For example, at a standard atmospheric pressure, nitrogen boils at −196° C. and demands an energy of 161 kJ per liter of liquid. The cooling process in the cryoneedle takes place as follows: the coolant enters the inlet tube of the cryoneedle at its liquid state; because of temperature differences, heat is transferred from the warm surrounding tissues through the cryoneedle tubes' walls to the coolant. This heat transfer causes energy release from the surrounding tissues, which lowers their temperature and essentially causes the formation of the ice-ball. On the other hand, the same heat transfer causes energy absorption in the coolant, which changes the coolant phase from liquid to gas. More and more energy is absorbed by the coolant as it flows, which continually contributes to the coolant phase change process. In case of a high flow rate, relative to the heat transfer from the surrounding tissue and the total length of the cryoneedle tubes, the coolant will not be transformed completely into gas inside the cryoprobe's tubes and therefore its balk temperature will be relatively close to the coolant boiling temperature. At relatively low flow rates, however, the phase change will be completed at some downstream point in the tubes, the boiling effect will vanish and the gas will warm up.

In general, liquid nitrogen is widely accepted as a coolant for cryosurgical applications since it has no side effects (79% of the air is nitrogen). Other cryogenic coolants may be used as well, such as liquefied air and liquefied helium, which boil at −178° C. and −267° C., respectively.

Figure 2:
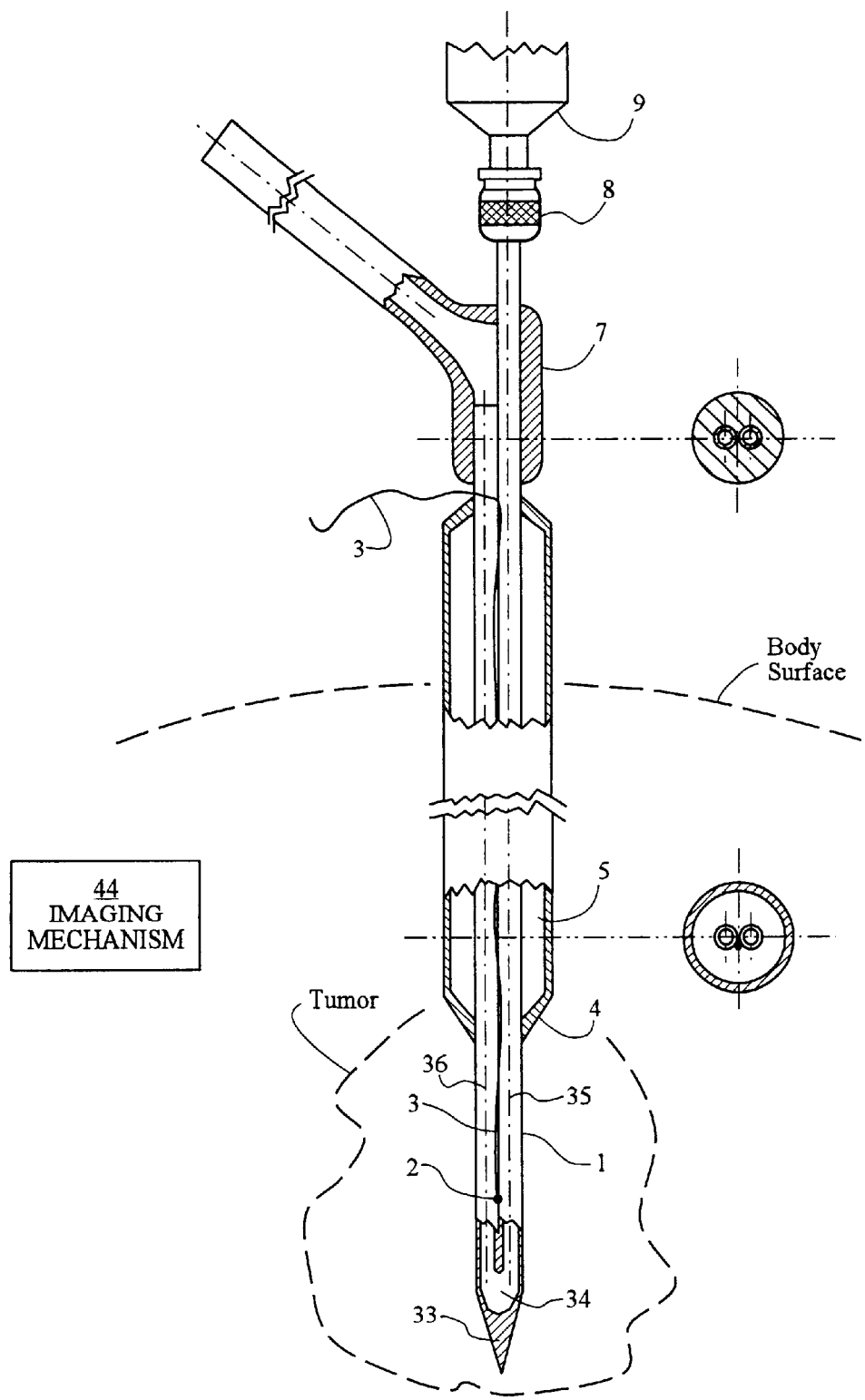
FIG. 2 is a side view of the cryoprobe B of the invention.

Cryoprobe B configuration, as shown in FIG. 2, is similar to cryoprobe A with the only exception that insulation shell 4 is rigidly connected to cryoneedle 1. Thermal insulation shell 4 contains thermal insulation material 5 such as minerals, gas, or vacuum. However, the preferable insulation technique is vacuum for both apparatus A and B. The cooling process in cryoprobes B is similar to that in cryoprobe A, as described above. All tubes' walls should be made as thin as possible. Using stainless steel, a wall thickness of 0.1 mm should be sufficient.

Three typical dimensions characterize the cryoprobe: (1) the diameter of the cryoneedle's inlet and outlet tubes; (2) the diameter of the thermal insulation; and (3) the length of the cryoprobe active surface. An outer diameter of 1 mm is sufficient for both the cryoneedle's inlet and outlet tubes, for some applications, in cases where stainless steel tubes with extra-thin walls are used (which have a wall thickness of 0.1 mm). However, the longer dimension of the cryoneedle cross section will be the sum of the diameters of the two adjacent tubes, i.e. 2 mm, in this case.

An outer diameter of 3.2 mm is sufficient for the thermal insulation shell, for the above case. Taking in account the thermal insulation wall thickness, this configuration should leave about 0.5 mm clearance from each side of the cryoneedle, in the direction of the longer dimension of the cryoneedle cross section. This clearance will provide a sufficient space for the vacuum to be effective as a thermal insulator.

It is noted that the 3.2 mm thermal insulation is not inserted all along the cryoneedle. Therefore, the cross section dimensions along the active cryoprobe surface are 1×2 mm, while along the thermal insulation the cryoprobe diameter is 3.2 mm. A cross section of 1×2 mm is about the smallest cryoprobe cross section available at this time.

The cryoneedle should be made of stainless steel for the general application of cryosurgery. However, for the special application of an MRI controlled cryosurgery, the cryoneedle should be made of copper or brass which are compatible with the MRI environment. In this case, the cryoneedle should be gold coated to protect the cryotreated tissue.

Currently, there is only one main well known concept for the design and construction of a boiling effect based cryoprobe, which was invented by Cooper at 1961. Cooper's approach is to place three tubes one inside the other, where the inner tube carries the coolant to the cryoprobe tip, the second tube carries the coolant gas back from the tip, and the space between the latter tube and the most outer tube is used for vacuum insulation.

The cryoprobe described herein has a very different configuration, which is based on a unshaped cryoneedle. The cryoneedle comprises two adjunct tubes and not one inside the other. One form of the cryoprobe (cryoprobe A of the invention) is assembled during the cryoprocedure which allows a minimal destruction to the cryotreated tissue, due to cryoprobe penetration, and an accurate localization of the cryoprobe tip 33.

The term "cryoneedle" is used herein for the presentation of the present invention, however, one must not be confused between this particular cryoneedle and a simple needle which carries a cryo-fluid. An ordinary needle has an inlet on one end and an outlet on the other end. The cryoneedle has the inlet in adjunct with its outlet, on the same end while the cryoprobe tip 33 is on the other end. The unique U-shape configuration of the cryoneedle requires a special design and construction for this particular application.

The term cryoneedle appears in the literature for two other but different applications: (1) for dermatology applications (Weshahy, A. H., 1993, "Interlesional Cryosurgery: A New Technique Using Cryoneedles", J. Dermatol. Surg. Oncol., Vol. 19, pp. 123–126), where a banded needle is inserted through the skin and below a tumor. In this case, the cryoneedle is a simple needle which carries a cryofluid. (2) For an application on hemorrhoids (Gao, X. K., Sun, D. K., Sha, R. J., Ding, Y. Sh., Yan, Q. Y., and Zhu, C. D., 1986, "Precooled, Spring-Driven Surgical Cryoneedle: A New Device for Cryohaemorrhoidectomy", Proceedings of the 11th International Cryogenic Engineering Conference, IECE 11, Berlin, West Germany, pp. 825–829, incorporated by reference herein), where a pre-cooled needle is inserted into an undesired tissue. The cryoneedle does not actually carry any cryofluid in the latter case.

One form of a pressurized cryofluid source is presented in FIG. 3. The cryofluid is contained in a thermal insulated container 11. Container 11 is pressurized by compressed air from air tank 15, through flexible air pressure pipe 13 and valve 14. Air tank 15 is pre-charged with compressed air by an external pressure source like an electric pump 31. Air tank 15 is designed to have much larger volume than cryofluid container 11. Therefore, the change in total gas volume during the entire cryosurgical operation is relatively small and is approximately the volume ratio of cryofluid container 11 to air tank 15. Under isothermal conditions, the total air pressure decrease will be proportional to the above volume ratio. However, this is not exactly the case since the air which enters container 11 contracts due to temperature decrease and therefore contributes to the overall pressure drop. Pressure decreases are compensated for by high pressure air tank 20. High pressure air tank 20 is connected to air tank 15, through pipe 19 and pressure regulator 18. Pressure regulator 18 keeps the pressure in air tank 15 on some set point. By analogy between fluid pressure and electrical potential, the setup of air tanks 15 and 20 can be viewed as a "pressure battery". The usage of air tank 20 is optional but not necessary. It is needed only when the volume ratio of air tank 15 to container 11 is not large enough, or in cases where a very accurate pressure control is required. The "pressure battery" may include the electric pump 31, or may be pre-charged by an external source.

Contrary to practice, the pressurized coolant system of the apparatus, as presented above, is separated into two main components: the coolant container 11 and the "pressure battery". This set-up has the following advantages: (1) the larger part of the system—the pressure battery—can be moved far from the cryosurgeon, possibly to another room, thus leaving more space in the operating room; (2) the coolant container is placed very close to the cryotreated tissue which reduces undesired coolant boiling along the feeding pipes. This reduces both the coolant consumption and the working pressure required to force the coolant through the feeding pipe. In turn, the reduction of the coolant consumption reduces the volume of the coolant container. Ordinary cryosurgery systems include the pressurized system and the coolant container in one unit.

Any ordinary air compressor could serve as an air pressure source for the cryofluid container 11. However, the air pressure system as presented here has advantages as a part of a surgical apparatus in that it can be very light in weight, small in dimension, very quiet in operation, and independent in power supply.

Practically, feeding tube 9 has to be as short as possible and therefore container 11 should be placed as close as possible to the cryotreated tissues. This can be compensated by a long air pressure pipe 13. This arrangement will decrease the heat losses along feeding tube 9 to the surroundings, which will decrease the required cryofluid flow rate, and which in turn will decrease the required volume of cryofluid container 11 for a specific operation. Low flow rates and short feeding tubes will require lower working pressures in the air pressure system. Furthermore, a smaller cryofluid container will require a smaller air tank volume. Moreover, the closer the cryofluid container is to the cryotreated tissues, the more compact apparatus 100 becomes in regard to dimensions and the safer the apparatus becomes in terms of pressure. One liter of coolant is generally needed for a triple cryoprobe operation, for a duration of 15 minutes under a pressure of 30 psi. A 2-liter vacuum insulated coolant container, a 34-liter low air pressure tank and a 22-liter high pressure air tank were used with the apparatus 100. However, the high pressure air tank was not needed for a single usage of the coolant container due to the high volume ratio of the low pressure air tank to the coolant container, as described above.

Before commencing the cryosurgery, the cryosurgeon will typically study the location, depth and configuration of the undesired tissues. The cryosurgeon will study the surrounding healthy tissues as well, and especially the vital tissues. This study can be performed via ultrasound, CT or MR imaging techniques. Based on this study, one or more appropriately configured cryoprobes will be chosen.

Figure 4:
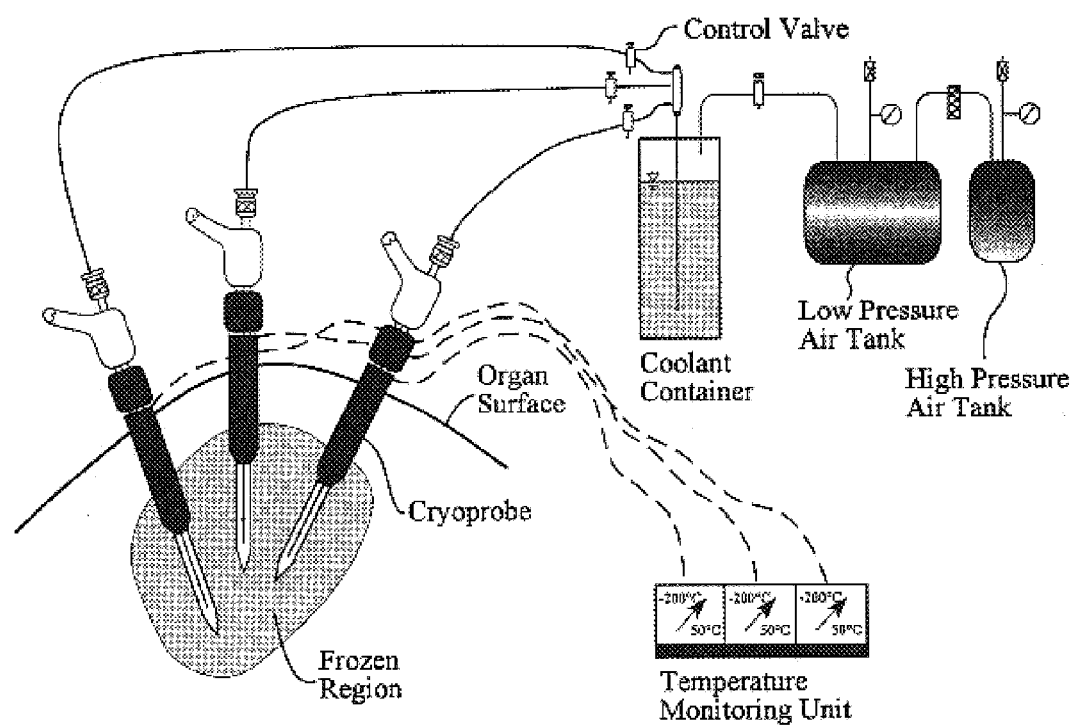
FIG. 4 is a schematic view of the cryosurgical apparatus with 3 cryoprobes.

A schematic view of the cryosurgical apparatus with 3 cryoprobes is shown in FIG. 4. The pressurized coolant source remains in the same configuration as for a single cryoprobe operation, as presented above. For a multi-cryoprobe, parallel feeding tubes lead the coolant to the cryoprobe and the temperature is monitored at the tip 33 of each cryoprobe separately. Each cryoprobe has a temperature sensor and a control valve on its feeding tube 9 in a multi-cryoprobe operation. All the cryoprobes flow rates are operated at the same technique presented above, at the beginning of the cryoprocedure. As cryosurgery proceeds, a need to reduce the cooling power of one or more cryoprobes may arise due to the presence of vital organs around the cryotreated tissue, or due to an irregularity in shape of the cryotreated tissue (tumor). At this stage, the cryosurgeon compares the frozen region formation with the cryotreated tissue shape via an imaging device such as ultrasound and operates the control valves accordingly.

Figure 5:
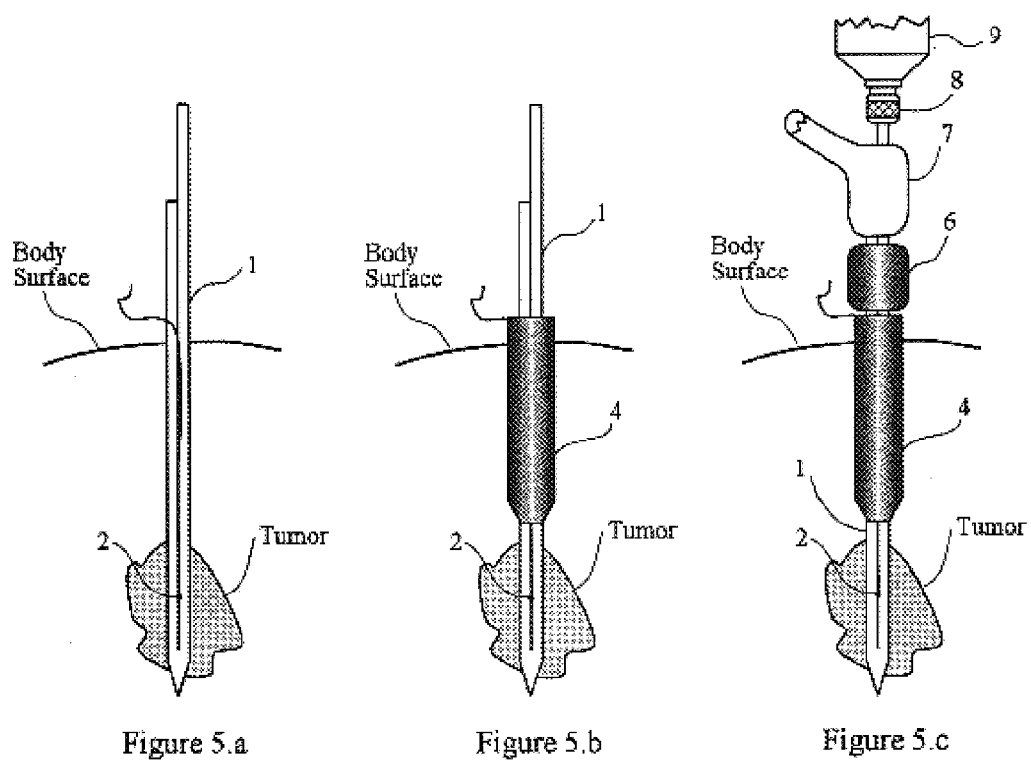
FIG. 5 is a diagrammatic representation showing some stages in cryoprobe insertion and localization.

The method of operation of cryoprobe A is addressed first. Utilizing a needle localization technique or a stereotactic localization technique, cryoneedle 1 will be inserted into the undesired tissue, as shown in FIG. 5a and as described hereafter. The fine diameter of the cryoneedle and its sharp pointed tip 33 are suitable for a straightforward insertion, without any cutting. The cryoneedle insertion procedure will be repeated in case of a multi-cryoprobe operation. Cryoneedles can be relocated at this stage with no significant damage to surrounding tissues.

The insertion of insulation shell 4 is next. Insulation shell 4 will be slide along cryoneedle 1 and will be inserted into the tissue, FIG. 5b. A small incision in the skin may be needed for the insertion of tube 4. The insertion of insulation tube 4 will be monitored by an imaging technique, to leave the appropriate cryoprobe active surface near the tip 33 of the cryoneedle. The other end of the insulation shell will remain outside of the body. The length of the insulation shell will be chosen for a particular cryotreatment according to the length of the cryoneedle, the depth of the undesired tissues, and the required cryoprobe active surface. Insertion of the insulation shell will be repeated in case of multi-cryoprobe operation.

Protection tube 6 will then be placed along cryoneedle 1, adjacent to insulation shell 4, FIG. 5c. Flexible vent tube 7 will be connected to the cryoneedle under a pressure fit. The length of protection tube 6 will be chosen to fit between insulation shell 4 and vent tube 7. Lastly, the inlet tube 35 of cryoneedle 1 will be connected to feeding tube 9 and the cryoprobe will be ready for operation. Container 11 will be filled with cryofluid and air tanks 15 and 20 will be charged with compressed air in advance.

The freezing stage is then started. While monitoring the frozen region formation, the cryosurgeon will operate the cryoprobe by means of valve 10. In case of a multi-cryoprobe operation, each cryoprobe will be controlled independently. The freezing process will continue until the entire target region is frozen, or until a danger of cryodestruction to surrounding tissues appears. Control valve 10 should be a standard needle valve which is designed for cryogenic temperatures. These valves are available in a wide range for commercial usage.

The thawing stage is then started. Thawing can be performed by either natural thawing, i.e. leaving the tissue to be thawed due to blood perfusion and metabolic activities, or by forcing warm fluid through the cryoprobe passageway, i.e. disconnecting the cryoneedle from feeding tube 9 and re-connecting it to a pressurized warm fluid source.

The cryoprobe(s) can now be cooled again, in case of repeated freezing/thawing cycles cryotreatment.

The method of operation of cryoprobe B is addressed next. The method of operation of cryoprobe B is similar to the method presented above for cryoprobe A with the only exception that cryoneedle 1 and thermal insulation shell 4 are inserted and extracted from the body together, as a one unit. This operation is suitable for cases in which the outer diameter of thermal insulation shell 4 is relatively small.

Any minimal-invasive cryoprocedure has to rely on an imaging technique such as ultrasound, CT or MRI. The ultrasound is widely accepted by cryosurgeons. The imaging technique is desired for two different tasks: (1) the localization of the cryoneedle(s), and (2) monitoring the cryolesion growth (the freezing front propagation). The uniqueness of the cryoneedle configuration of the invention, as being assembled during the cryoprocedure and/or as having small dimensions, offers a major advantage for an easy and precise localization of the tip 33. Two cryoneedle localization techniques are discussed below: needle localization and stereotactic.

Needle localization technique: This technique is currently used for guidance of the surgeon to the tumor, and towards the extraction of a tumor of the breast, as follows. First, the tumor is located on the ultrasound image. Then, monitored by the ultrasound, a needle is inserted into the center of the tumor (while the patient is treated with a local anaesthesia). Lastly, the patient is transferred to the operation room and a surgery is performed to extract the tumor. The tumor is found by dissecting along the needle.

Localization of a standard cryoprobe by means of the needle localization technique should be performed as described above, where a pathway for the cryoneedle is dissected along the needle.

Localization of the cryoneedle of the invention by means of the needle localization technique is performed in one of the two alternative ways: (1) By using the cryoneedle as the needle for the needle localization procedure. (2) First by inserting the standard needle, and then by replacing it with the cryoneedle. In both cases, a pathway is not needed for the cryoneedle, however, a small incision may be required on the skin. The apparatus will be assembled after the localization of the cryoneedle, in situ, as described above.

Stereotactic localization technique: The cryoneedle is guided to the tumor by stereotactic technique. This requires the use of a stereotactic breast imaging/biopsy table which provides digital mammographic images of the breast. The cryoneedle is mounted on a needle holder which is mounted on the stereotactic table. Using computer generated coordinates obtained from a stereo images, the biopsy needle or cryoneedle is positioned into the tumor and therapy is carried out. This can be performed under a local anaesthesia. In this case, the cryoneedle has to be designed to be compatible, in size and shape, with the standard biopsy needle used with the stereotactic device. The apparatus will then be assembled, in situ, as described above.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for freezing tissues comprising the steps of:
   inserting a cryoneedle having a diameter of less than 5 mm into a patient's body, the cryoneedle has a sharp pointed tip, an inlet tube and an outlet tube disposed alongside the inlet tube, and a u-shaped channel connector connected to the inlet tube and the outlet tube through which cryofluid from the inlet tube flows to the outlet tube;
   sliding an insulation shell in place over a predetermined portion of the cryoneedle in the body of the patient; and
   flowing cryofluid into the inlet tube, through the channel connector and out of the cryoneedle through the outlet tube.

2. A method as described in claim 1 wherein the flowing step includes the step of flowing cryofluid through the cryoneedle and venting the cryofluid into the environment.

3. A method as described in claim 2 including after the sliding step, there is the step of sliding a protection tube in place over the cryoneedle until it is adjacent to the shell but the protection tube is outside the patient's body.

4. A method as described in claim 3 wherein the flowing step includes the step of flowing the cryofluid out of the cryoneedle to a vent connected to the outlet tube.

5. A method as described in claim 4 including the step of sensing the temperature of the cryoneedle with a temperature sensor disposed adjacent the tip and in contact with the cryoneedle.

6. A method as described in claim 5 wherein the inserting step includes the step of inserting the cryoneedle which is made of copper or brass and is gold coated.

7. A method as described in claim 2 wherein the inserting step includes the step of inserting the cryoneedle with an insulation shell positioned about the cryoneedle at a predetermined location simultaneously into the body of the patient.

8. A method as described in claim 2 wherein the inserting step includes the step of imaging the cryoneedle as it is inserted into the patient's body.

9. A method as described in claim 4 including the step of sensing the temperature of the cryoneedle with a temperature sensor disposed adjacent the tip and in contact with the cryoneedle.

10. A method as described in claim 9 wherein the inserting step includes the step of inserting the cryoneedle which is made of copper or brass and is gold coated.

11. A method for freezing breast tissue of a patient comprising the steps of:

forming images of the breast of the patient;

generating with a computer aided coordinates to position a cryoprobe having a cryoneedle having a diameter of less than 5 mm in the breast of the patient, the cryoneedle has a sharp pointed tip, an inlet tube and an outlet tube disposed alongside the inlet tube, and a u-shaped channel connector connected to the inlet tube and the outlet tube through which cryofluid from the inlet tube flows to the outlet tube;

guiding the cryoprobe into the breast of the patient based on how the cryoprobe appears in the images and the computer aided coordinates;

sliding an insulation shell in place over a predetermined portion of a cryoneedle in the body of the patient; and flowing cryofluid into the inlet tube, through the channel connector and out of the cryoneedle through the outlet tube.

12. A method as described in claim 11 wherein the forming step includes the step of forming stereotactic images of the breast of the patient.

13. A method as described in claim 12 wherein the guiding step includes the step of placing the cryoprobe into a needle holder, and guiding the cryoprobe along the needle holder into the patient.

14. A method as described in claim 13 including after the guiding step, there is the step of monitoring cryolesion growth.

* * * * *